United States Patent [19]

Manghisi et al.

[11] 4,262,006

[45] Apr. 14, 1981

[54] SUBSTITUTED 2-PHENYLAMINO-IMIDAZOLINES-(2) AND PHARMACEUTICAL COMPOSITIONS CONTAINING THEM

[75] Inventors: Elso Manghisi; Giuseppe Cascio, both of Monza; Giancarlo B. Fregnan, Milan; Giovanni Ferni, Cusano, all of Italy

[73] Assignee: Istituto Lusofarmaco d'Italia s.p.a., Milan, Italy

[21] Appl. No.: 100,833

[22] Filed: Dec. 6, 1979

[30] Foreign Application Priority Data

Dec. 12, 1978 [IT] Italy ............................... 30738 A/78
Nov. 12, 1979 [IT] Italy ............................... 27202 A/79

[51] Int. Cl.³ .................. A61K 31/415; C07D 405/02
[52] U.S. Cl. ................................. 424/273 R; 548/348
[58] Field of Search ..................... 548/348; 424/273 R

[56] References Cited

U.S. PATENT DOCUMENTS 3,850,926  11/1974  Stähle et al. ......................... 548/348

Primary Examiner—John D. Randolph
Assistant Examiner—Jane T. Fan
Attorney, Agent, or Firm—Bucknam and Archer

[57] ABSTRACT

The invention provides novel substituted 2-phenylamino-imidazolines-(2) having hypotensive, bradycardizing and diuretic activities.

7 Claims, No Drawings

SUBSTITUTED 2-PHENYLAMINO-IMIDAZOLINES-(2) AND PHARMACEUTICAL COMPOSITIONS CONTAINING THEM

This invention concerns a series of substituted 2-phenylamino-imidazolines-(2), of general formula (I)

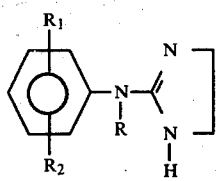

and their pharmaceutically acceptable salts.

In the formula (I), R represents the residue

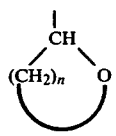

in which n represents 3 or 4; $R_1$ and $R_2$, which may be the same or different, each represent hydrogen, fluorine or chlorine or bromine, or a lower alkyl group having 1–4 carbon atoms.

The invention also relates to pharmaceutical compositions having hypotensive, bradycardizing and diuretic activity, containing as active principles one or more compounds of formula (I). The invention also concerns processes for the preparation of compounds of the formula (I).

The compounds (I) can be obtained by reacting a 2-phenylimino-imidazolidine of formula (II)

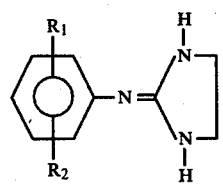

or its sodium salt, with a compound of formula (III) or (IV)

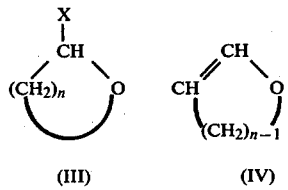

in which n is as hereinbefore defined and X represents an halogen atom (chlorine, bromine), a lower alkoxy group or a lower acyloxy group. The compounds (III) and (IV) used in the pure state or prepared "in situ" according to the methods well-known in the literature. (Recl.Trav.Chim.Pays-Bas 98,371–380, 1979).

When X represents an halogen atom, the reaction is carried out in polar or non-polar solvents, at a temperature ranging from −50° C. to room temperature. When X is an alkoxy or an acyloxy group, or when the compounds (IV) are used, the reaction is carried out in dimethylformamide or in acetonitrile at the boiling point of the solvents.

Salts can be prepared from the compounds of general formula (I) with pharmaceutically acceptable inorganic acids, for example hydrochloric, hydrobromic, nitric, sulphuric, or phosphoric acid, or with organic carboxylic acids, for example acetic, propionic, glycolic, malonic, succinic, maleic, hydroxymaleic, fumaric, malic, tartaric, citric, glucuronic, benzoic, mandelic, salicylic, 4-aminosalicylic, 2-phenoxybenzoic, pamoic, nicotinic, or isonicotinic acid, or using sulphonic organic acids, for example methanesulphonic, ethanesulphonic, 2-hydroxyethanesulphonic, ethane-1,2-disulphonic, p-toluene-sulphonic, or naphthalene 2-sulphonic acid.

The compounds of general formula (I) and their acid addition salts are stable at 37° C. both in the simulated gastric juice and in the intestinal juice.

The new compounds, like their acid addition salts, are endowed with a remarkable hypotensive, bradycardizing and diuretic activity. The doses to be used orally in human theraphy range from 0.3 to 100 mg.

The new compounds have some advantages as compared with their respective precursors (compounds of general formula (I) in which R=H); particularly 2-[N-2,6-dichlorophenyl-N-(2-tetrahydropyranyl)amino]-imidazoline-(2) and 2-[N-(2,6-dichlorophenyl)-N-(2-tetrahydrofuranyl)amino]-imidazoline-(2) show several advantages as compared with 2-(2,6-dichloroanilino)—$\Delta^2$-imidazoline (Clonidin).

Even at doses superior than those indicated in the following tables, they do not alter the behaviour of the animal; moreover, they are lacking of both stimulating and inhibiting properties on the α-adrenergic receptors and the parasympathetic system.

The compound n. 1, besides showing, in the animal, a more effective and lasting hypotensive activity than Clonidin itself (table I), shows a more favourable behaviour in those tests displaying possible side effects.

Table I shows that Clonidin, administered orally to the rat, causes initial pressure rises, showing peripheric α-adrenergic activity, which property is considered undesirable in the clinic literature (HUNYOR Ser. No. et al. Brit. Med., 4, 23 (1975) WING L.M.H. et al. Brit. Med., 1 136 (1977)); on the contrary, this hypertensive phase is absent after equivalent doses of compund n.1.

Moreover, the administration of 5 μM/kg of Clonidin to the awake dog induces—after an initial arterial pressure decrease, lasting 90 minutes—a remarkable rise of the arterial pressure, with symptoms of restlessness and tremors, symptoms which can be compared to the "rebound" hypertensive crisis observed in man (LESLEY MATIER W. and COMER W. T., Annual Reports in Medicinal Chemistry, 13 (1978) Chapter 8—Antihypertensive agents, pages 71 and 72); the same dose of compound 1, on the contrary show in the dog only a lasting hypotensive activity.

Finally, the compound n.1 is 40 and respectively 800 times less active than Clonidin in reducing the spontaneous motility respectively in the rat and in the mouse (table IV), showing therefore a virtually insignificant sedative activity; this activity is undesirable in man (LESLEY MATIER W. and COMER W. T. 1978).

The compounds according to the invention may be administered orally, by injection or rectally using suitable pharmaceutical formulations in solid, liquid or suspension form (tablets, capsules, phials, syrups, suppositories and so on).

The following, not-limiting tables summarize the pharmacological characteristics of the compound n.1, that is 2-[N-(2,6-dichlorophenyl)-N-(2-tetrahydropyranyl)amino]-imidazoline-(2), and of compound n.2, that is 2-[N-(2,6-dichlorophenyl)-N-(tetrahydrofuranyl)amino]imidazoline-(2).

METHODS

The hypotensive and bradycardizing activities have been studied in the awake rat and dog by means of chronic incannulation respectively of the carotid and of the saphena artery and continuous registration by means of transducers.

The diuretic activity has been studied in the awake rat under hydric load (physiological solution 25 ml/kg, orally).

TABLE I

| Com-Pounds | dose $\mu M/kg$, orally | Arterious pressure variation | | | |
|---|---|---|---|---|---|
| | | rat | | dog | |
| | | % (mmHg) | duration* (mmHg) | % (mmHg) | duration* (mmHg) |
| No 1 | 1 | −14 | 190 | −16 | 305 |
| | 5 | −19 | >320 | −17 | 325 |
| No 2 | 1 | −8 | 210 | — | — |
| | 5 | −14 | >380 | — | — |
| Clonidin** | 1 | +27/−11 | 45/150 | −12 | 60 |
| | 5 | +27/−19 | 39/>320 | −16/+45 | 90/120 |

*50% recovery
**2-[(2,6-dichlorophenyl) amino]-imidazoline-(2).

TABLE II

| | | CARDIAC FREQUENCY VARIATION | | | |
|---|---|---|---|---|---|
| Compounds | dose $\mu M/kg$, orally | rat % (b/min) | duration (min) | dog % (b/min) | duration (min) |
| No 1 | 1 | −10 | 200 | −40 | 365 |
| | 5 | −16 | >360 | −50 | >400 |
| No 2 | 1 | −13 | 210 | — | — |
| | 5 | −15 | >380 | — | — |
| Clonidin | 1 | −13 | 160 | −45 | 250 |
| | 5 | −41 | >360 | −66 | >400 | b/min = beats/minute

TABLE III

| Compounds | dose $\mu M/kg$ orally | DIURETIC ACITIVITY % of increasing of the urinary volume |
|---|---|---|
| No 1 | 1 | 74 |
| | 5 | 184 |
| No 2 | 1 | 155 |
| | 5 | 235 |
| Clonidin | 1 | 220 |
| | 5 | 2 |

TABLE IV

| | DECREASE OF THE SPONTANEOUS MOTILITY ($ED_{50}$ $\mu M/kg$ orally) | |
|---|---|---|
| Compounds | mouse | rat |
| No 1 | 80 | 10 |
| No 2 | 20 | 66 |
| Clonidin | 0.095 | 0.26 |

The following examples illustrate the invention, without restricting it.

The melting points are not correct. The identity and purity of the substances were checked by means of elemental analysis of C,H,N and Cl, infra-red, N.M.R. and U.V. spectra.

EXAMPLE 1

2-[N-(2,6-dichlorophenyl)-N-(2-tetrahydropyranyl)amino]imidazoline-(2)

To a solution of 2.46 gr (10.2 millimoles) of 2-(2,6-dichlororophenylimino)-imidazolidine in 60 ml of anhydrous methylene chloride, under stirring at room temperature, 0.28 gr (12.24 millimoles) of NaH are slowly added. After the addition, the solution is stirred again for 60 minutes, then cooled at −40° C. and a solution of 1.6 gr (13.26 millimoles) of 2-chloro-tetrahydropyrane in 2 ml of anhydrous methylene chloride are added drop by drop. After the addition the cooling bath is removed and room temperature is reached. After filtration, the solution is washed with a diluted solution of NH₄OH, then dried on Na₂SO₄ and evaporated to dryness at reduced pressure. M.p.=122°−3° C. (from hexane).

In similar way are prepared:

2-[N-(2,6-dichlorophenyl)-N-(2-tetrahydrofuranyl)amino]-imidazoline-(2), m.p.=71°−2° C. (from diisopropyl ether).

2-[N-(2-chloro-4-methylphenyl)-N-(2-tetrahydropyranyl)amino]-imidazoline-(2), m.p.=135°−137° C. (from hexane).

2-[N-(2-methyl-5-fluorophenyl)-N-(2-tetrahydropyranyl)amino]-imidazoline-(2), m.p.=125°−127° C. (from hexane).

2-[N-(2,6-diethylphenyl)-N-(2-tetrahydropyranyl)amino]-imidazoline-(2), m.p.=135°−140° C. (from hexane).

We claim:

1. A substituted 2-Phenylamino-(2)-imidazoline of formula (I)

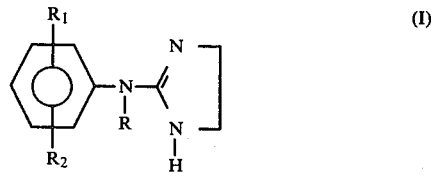

and a pharmaceutically acceptable salt thereof in which R is the radical

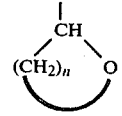

in which n may be 3 or 4, and $R_1$ and $R_2$, which are the same or different, are each hydrogen, fluorine, chlorine, bromine or alkyl of 1 to 4 carbon atoms.

2. A compound according to claim 1, which is 2-[N-(2,6-dichlorophenyl)-N-(tetrahydropyranyl)amino]-imidazoline-(2) and a pharmaceutically acceptable salt thereof.

3. A compound according to claim 1, which is 2-[N-(2,6-dichlorophenyl)-N-(2-tetrahydrofuranyl)amino]- imidazoline-(2) and a pharmaceutically acceptable salt thereof.

4. A compound according to claim 1, which is 2-[N-(2-chloro-4-methylphenyl)-N-(2-tetrahydropyranyl)amino]-imidazoline-(2) and a pharmaceutically acceptable salt thereof.

5. A compound according to claim 1, which is 2-[N-(2-methyl-5-fluorophenyl)-N-(2-tetrahydropyranyl)amino]-imidazoline-(2) and a pharmaceutically acceptable salt thereof.

6. A compound according to claim 1, which is 2-[N-(2,6-diethylphenyl)-N-(2-tetrahydropyranyl)amino]-imidazoline-(2) and a pharmaceutically acceptable salt thereof.

7. A pharmaceutical composition with hypotensive, bradycardizing, diuretic activities, comprising an effective amount of a compound, according to claim 1, in form of the free base or a pharmaceutically acceptable salt thereof and a pharmaceutically acceptable carrier.

* * * * *